Feb. 11, 1964 V. A. RENNER Plant Pat. 2,364

BLUEGRASS PLANT

Filed Jan. 22, 1963 3 Sheets-Sheet 1

Inventor
Victor A. Renner

Strauch, Nolan & Neale
Attorneys

BLUEGRASS PLANT

Filed Jan. 22, 1963 3 Sheets-Sheet 2

Inventor
Victor A. Renner

Strauch, Nolan & Neale
Attorneys

BLUEGRASS PLANT

Filed Jan. 22, 1963 3 Sheets-Sheet 3

Inventor
Victor A. Renner
Strauch, Nolan & Neale
Attorneys

United States Patent Office

Plant Pat. 2,364
Patented Feb. 11, 1964

2,364
BLUEGRASS PLANT

Victor A. Renner, Marysville, Ohio, assignor to The O. M. Scott & Sons Co., Marysville, Ohio, a corporation of Ohio Filed Jan. 22, 1963, Ser. No. 253,234
1 Claim. (Cl. Plt.—88)

The present invention relates to a new and perennial Kentucky bluegrass plant which was discovered by me in an area adjacent to my home lawn near Marysville, Ohio. A dark green colony of grass with novel growth characteristics was observed in an area adjacent to the lawn of my home at a time when the rest of the turf was yellowed due to disease and dryness. Plant material from this spot was taken to the greenhouse for observation and for vegetative reproduction of additional plants. After growth in the greenhouse, plants vegetatively reproduced from the parent plants were installed in field plots for both turf evaluation and plant increase. The plants were labeled "S–2" Kentucky bluegrass.

S–2 bluegrass has several distinctive characteristics not evident in other bluegrasses, the most desirable of which is its persistent deep color in comparison to other bluegrasses in the spring and through periods when foliar diseases are active. Others are its low growth properties, high density and tolerance to close mowing as compared with Common Kentucky bluegrass, high degree of resistance to Helminthosporium leaf spot and leaf and stem rust, ability to become well established in regions where cool-season grasses are used for turf purposes, and a high degree of tolerance to commercial pesticide formulations containing chlorinated hydrocarbons, organic mercury compounds and chlorophenoxy herbicides.

The outstanding tolerance of S–2 bluegrass to leaf spot disease contributes materially to its excellent performance through hot weather under drought conditions. This characteristic is of importance to subsequent vigor of the plant throughout the season. Its inherent resistance to foliar diseases extends to the season of grass enjoyment and lessens the maintenance procedures and costs of providing fungicides for protecting against these diseases.

S–2 bluegrass produces less vertical growth than most other bluegrasses during periods when bluegrasses normally produce excessive flushes of growth. This characteristic is a definite advantage as it reduces the mowing required to maintain a well-groomed lawn. The slower rate of vertical growth reduces clipping yields; thereby reducing the volume of clippings to be removed by raking or sweeping. Less vertical growth also reduces the possibility of scalping or defoliation of the lawn when mowing is infrequent.

S–2 bluegrass develops a dense turf under mowing and has a pleasing texture. It is a vigourous competitor and is compatible with other cool season grasses. Its dense growth suppresses weed encroachment and imparts ruggedness and good traffic-wearing qualities. Furthermore, its high density provides a cushion-like resilience which is most desirable.

It is therefore, the primary object of the present invention to provide a bluegrass plant having the desirable characteristics aforementioned and to be described in detail below. Other objects will become apparent to those skilled in this art from the appended claim and following description in connection with the accompanying illustrations wherein:

PLANT DESCRIPTION

Figure 1:
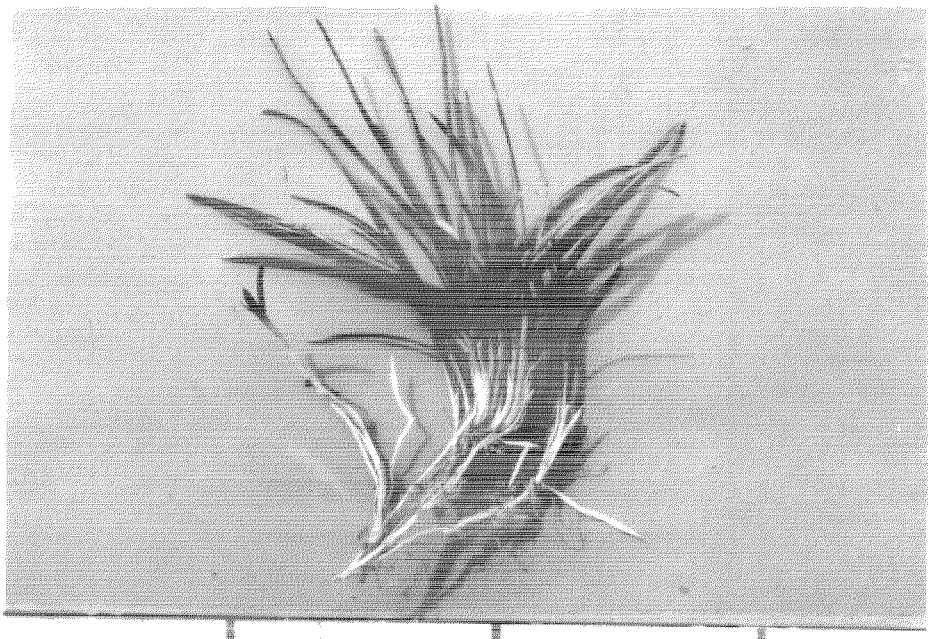
FIGURE 1 illustrates tillers and rhizomes removed from an S–2 bluegrass plant eight months after planting.
Figure 2:
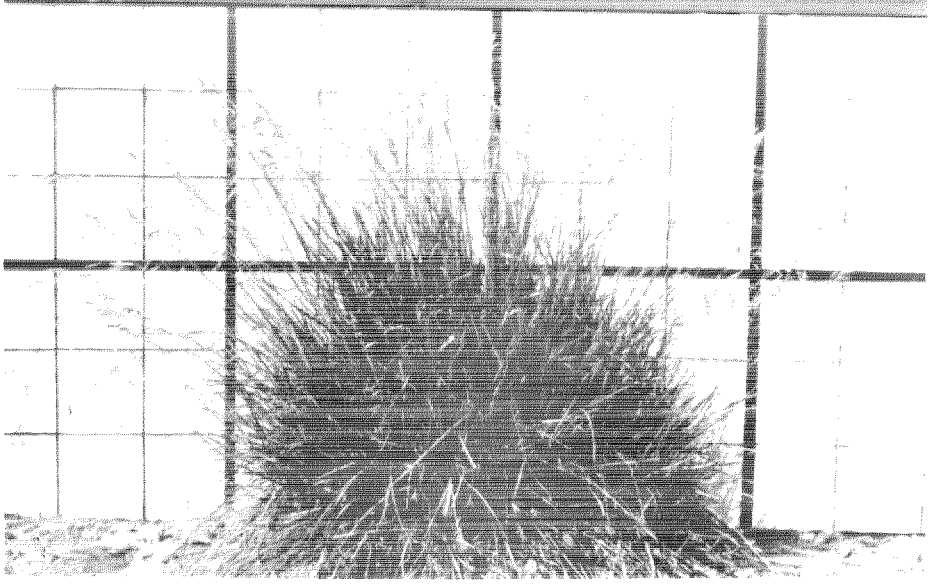
FIGURE 2 illustrates a mature S–2 bluegrass plant.
Figure 3:
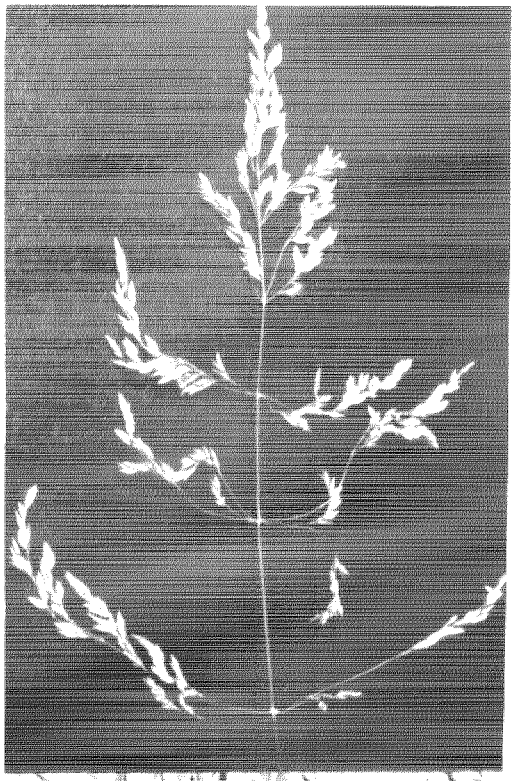
FIGURE 3 shows a mature S–2 bluegrass panicle.

S–2 Kentucky bluegrass (*Poa pratensis*) is characterized by tufted culms, erect 20 to 30 inches tall when undisturbed by clipping. Sheaths somewhat keeled; ligule slightly longer than found for Common Kentucky bluegrass in measurements made on this variety in plots in Marysville, Ohio in June 1962. Leaf blades 2 to 4 mm. wide, flat or folded; the basal blades are often elongated. Panicle 70 to 130 mm. pyramidal or oblong pyramidal open, the lowermost branches in whorls of 3 to 5, ascending or spreading, naked below; spikelets crowded, 2 to 6 flowered, 3 to 6 mm. long; lemmas webbed at base, pubescent on lower two-thirds of keel and lower half of marginal nerves, intermediate nerves glabrous. Tillering characteristics; the mature plant and panicle, mature florets, and spikelets of S–2 are shown in FIGURES 1, 2, 3, 4, 5 and 6. Since environmental conditions such as climate and soil influence morphological characteristics to some degree, the morphological characteristics will vary slightly. Morphological characteristics of S–2 Kentucky bluegrass as compared to Delta and Common Kentucky bluegrass are given in Table 1 below.

GROWTH BEHAVIOR

Vertical growth measurements for S–2 and other bluegrasses are given in Table 2. The data shows the average 7-day accumulated vertical growth of S–2 to be significantly less than Delta and Common Kentucky bluegrass each month from May through September. Vertical growth of S–2 and Merion Kentucky bluegrass was approximately the same up to September. During September significantly less grass clippings were produced on S–2 as compared to Merion.

Data are given in Tables 3 and 4, showing amounts of grass clippings removed over a four month period during 1961 and a five month period during 1962. The recorded data represents average 7-day accumulated clipping samples and shows S–2 to produce significantly less growth in terms of grass clippings removed than Merion and Common Kentucky bluegrass during the 1961 season. The amount of grass clippings removed for S–2 and Delta did not differ significantly during 1961, however, during 1962, S–2 produced fewer clippings than Delta or Merion when comparisons between means were made on a seasonal basis (Table 4).

The vertical growth data and grass clippings data indicate the inherent characteristic of S–2 to produce less foliar growth at standard lawn mowing heights, thus providing a definite advantage to the homeowner in reducing the amount of grass clippings to be removed from lawn areas after mowing. Further, low vertical growth minimizes the number of times mowing is required during the season. This is an important feature as mowing is the biggest chore in lawn maintenance. Another benefit of the growth characteristic of S–2 is emphasized in Table 5. As the data show, when 14-day accumulated growth was measured, significantly less grass clippings were produced by S–2.

DISEASE RESISTANCE

A comparison of S–2 and other bluegrasses for resistance to leaf spot (*Helminthosporium spp.*), stem rust (*Puccinia graminis*), and dollar spot (*Sclerotinia homoeo-*

*carpa*) are given in Tables 6, 7 and 8. The data presented in Table 6 were compiled from two independent experiments for the respective periods 1960–1961 and 1960–1961–1962. Data on stem rust are from two experiments evaluated in 1961 and data on dollar spot are from one experiment over a two year period.

S–2 shows a significantly higher level of resistance to leaf spot than Delta and Common Kentucky bluegrass in both experiments (Table 6) over a three year period. The data for stem rust reaction shows S–2 to possess a significantly higher level of resistance than Merion bluegrass (Table 7). Over a two year period it was found that S–2 has a relatively good level of resistance to dollar spot disease (Table 8).

TURF DENSITY

Data compiled for turf density are given in Tables 9 and 10. The density ratings (Table 9) were made over a two year period on turf variety performance plots clipped at two inch height. The data show S–2 to maintain a high turf density throughout 1961 and 1962. Quantitative plant counts listed in Table 10 that were taken from two year old sod show S–2 to have a significantly higher plant density for a given area than other bluegrass varieties evaluated.

TURF COLOR

Data compiled during 1960, 1961 and 1962 on turf color for S–2 and other bluegrass varieties are given in Tables 11 and 12. The results for the two independent studies show S–2 to rank very well in the maintenance of color for each season.

Figure 7:
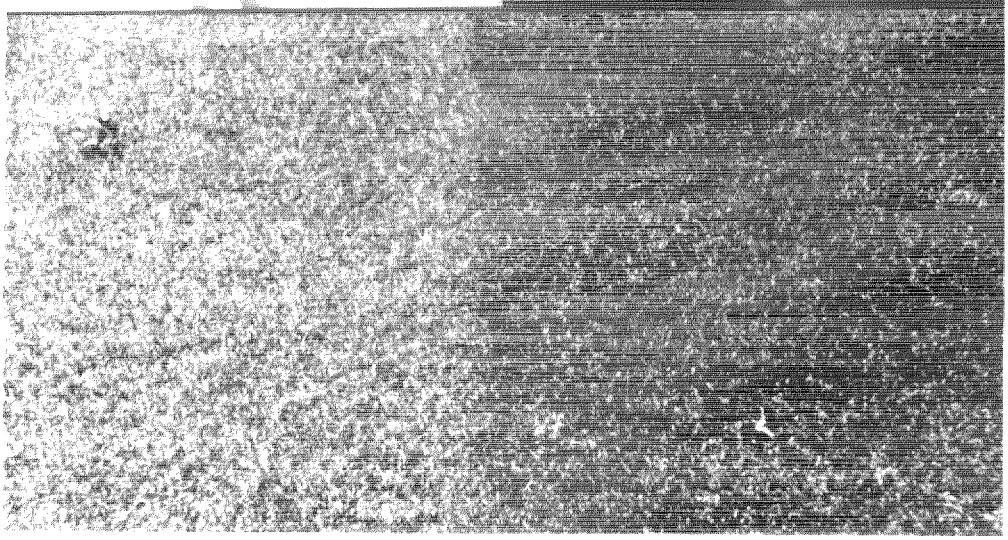
FIGURE 7 illustrates the contrast in early spring color between Park Kentucky bluegrass on the left, and S–2 Kentucky bluegrass on the right.

S–2 foliage color is characteristically an intense dark green as contrasted to Delta Kentucky bluegrass foliage which is considered a light green. A spring color comparison between S–2 and Park Kentucky bluegrass is shown in FIGURE 7.

LEAF TEXTURE

S–2 has been consistently classified as medium in leaf texture—slightly finer than Merion Kentucky bluegrass, but coarser than Delta and Common Kentucky bluegrass.

DROUGHT AND CHEMICAL TOLERANCE

Ratings made during hot dry conditions on levels of wilting as reflected in brown foliage condition and "tracking" indicated that S–2 and Merion Kentucky bluegrass were affected to a lesser degree than Delta and Common as shown in data recorded in table 13. Early-season damage from leaf spot disease sustained by Delta and Common Kentucky bluegrass on the same plots that showed early wilting from moisture stress perhaps contributed to this condition. S–2 and Merion, in contrast, were not influenced materially by early-season leaf spot disease and thus, were no doubt less susceptible to drought conditions.

Organic mercurial fungicides used widely for preventing and controlling diseases of turgrasses have been found to severely discolor and damage Merion Kentucky bluegrass while S–2 has been found to be highly tolerant of such fungicides. Tolerance to organic mercurial fungicides or fungicides containing this chemical as a component is of considerable importance since the organic mercurials have a high level of fungicidal activity and are used widely in different commercial fungicide formulations.

S–2 Kentucky bluegrass has also shown a high level of tolerance to chlorophenoxy herbicides including 2,4-dichlorophenoxy acetic acid and 2,4,5-trichlorophenoxy acetic and propionic acid. S–2 in addition has been observed to have excellent tolerance to chlorinated hydrocarbons and other commonly used pesticides.

FLORET-CARYOPSIS CHARACTERISTICS

Data for the number of caryopses with attached lemma and palea per pound recorded for S–2 and other bluegrass varieties are given in Table 14. A standard error value calculated for comparing the mean count for S–2 with each of the other bluegrass varieties shows the mean of S–2 to differ significantly from Merion, Delta and Newport. The test of significance further indicated no difference in number of caryopses per pound between S–2, Common and Beaumont Kentucky bluegrass.

CYTOLOGICAL CHARACTERISTICS

The results of preliminary cytological studies have shown the chromosome number of S–2 to be approximately 86 unreduced. This is in contrast to chromosome numbers of 71 and 81 found for Delta and Newport respectively.

REPRODUCTION AND PROPAGATION

The two broad categories of apomictic reproduction are classified as agamospermy (reproduction by means of disseminules or modified caryopses) and vegetative reproduction (reproduction by means of propagules as rhizomes). Both broad categories of apomixis are classified as asexual reproduction. S–2 bluegrass is reproduced asexually both by agamospermy and by vegetative reproduction. All asexually reproduced S–2 bluegrass offspring shows complete conformity with the mother plant. S–2 cannot be sexually reproduced; i.e., it cannot be reproduced from true seeds. S–2 bluegrass is, therefore, 100% asexually reproduced.

A complete review of apomixis appears in Apomixis in Higher Plants by Ake Gustafsson, published in G W K Gleerup, Lund, Sweden 1946.

Asexual reproduction of S–2 by propagules (rhizomes) and by disseminules (modified caryopses) has been found to produce genetically uniform plants indistinguishable from the maternal plant in morphological characteristics and growth behaviour through successive generations of propagation.

Figure 4:
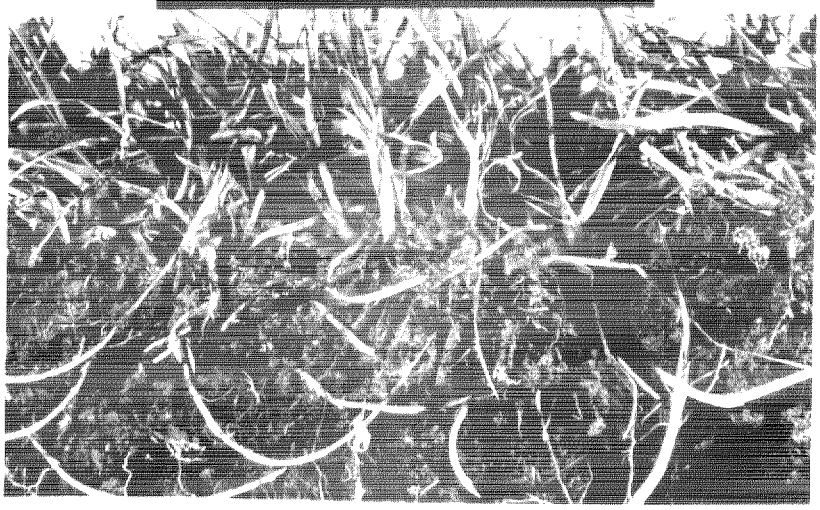
FIGURE 4 illustrates rhizome development of S–2 bluegrass.
Figure 5:
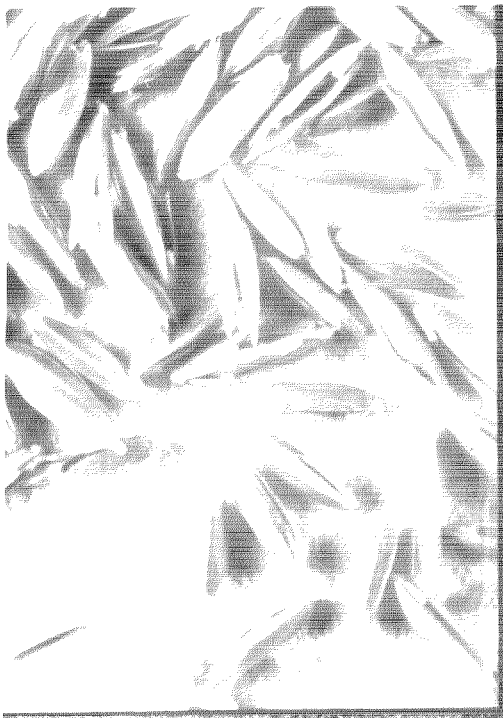
FIGURE 5 shows a group of S–2 Kentucky bluegrass florets.
Figure 6:
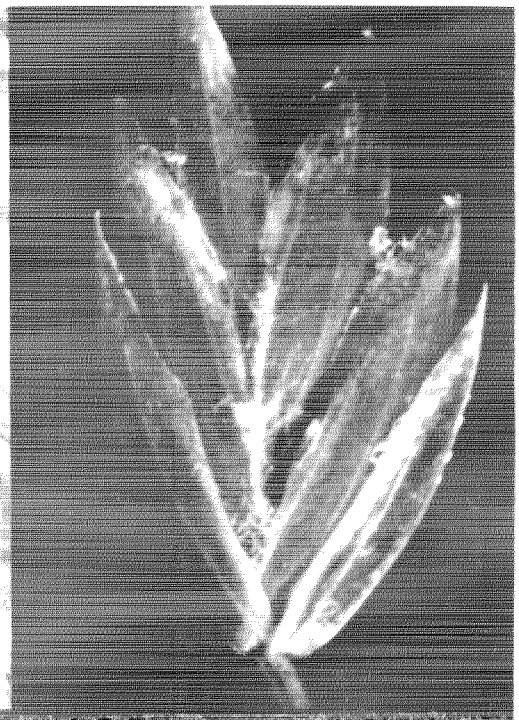
FIGURE 6 shows a mature spikelet of S–2 Kentucky bluegrass.

Lateral growth of individual propagules after one season is sufficient to cover an area 8 to 10 inches in diameter under routine lawn maintenance procedures. Lateral spread of S–2 plants occurs by modified shoots termed rhizomes growing from basal internodes of the primary plant. The extensive rhizome system of S–2 that facilitates vegetative reproduction is shown in FIGURE 4.

Reproduction of S–2 by disseminules (modified caryopses) represents another distinct asexual method of reproduction. By this method, disseminules are derived from sporophytes arising from gametophytes without union of male and femal nuclei. The gametophyte develops by apospory which means it is produced either from an embryo-mother-cell or its derivatives, or from a somatic cell. The disseminules (modified caryopses) that are produced contain an endosperm and embryo plant identical to the maternal plant. This method as with propagules results in the reproduction of plants generation after generation identical to the parent plant genetically and in external morphological characteristics.

The propagation of S–2 by disseminules offers the same advantages as propagation by true seeds. The modified caryopses resembles a true seed in external and internal morphological characteristics yet differs cytologically in that the embryo plant carries only the material chromosome complement as is the case in strict vegetative reproduction.

The very frequent occurrence of plants that develop from a true seed are easily identifiable and are removed from foundation seed fields before harvesting. To facilitate removal of aberrant plants, plantings are made in rows. Intensive roguing is then carried out before production fields are harvested.

*Table 1.—Morphological Comparison of S-2 and Other Bluegrasses—1962*

| Variety | Morphological characteristics | | | | | | | |
|---|---|---|---|---|---|---|---|---|
| | Plant height, in. | Florets/Spikelets | Lemma length, mm. | Glume length, mm. | | Panicle length, mm. | Width leaf blade, mm. | Ligule length, mm. |
| | | | | 1st | 2nd | | | |
| S-2 | 20.6 | 2.8 | 2.3 | 2.1 | 1.8 | 99.6 | 3.3 | .36 |
| Delta | 24.3 | 2.3 | 2.5 | 2.7 | 1.9 | 84.6 | 3.0 | .25 |
| Common | 26.1 | 2.2 | 2.6 | 2.3 | 1.9 | 89.0 | 2.1 | .27 |

*Table 2.—Monthly Average Vertical Growth of S-2 and Other Bluegrasses Mowed at 1⅜ Inch Height Weekly—1962*

| Variety | Vertical growth (mm.) | | | | | |
|---|---|---|---|---|---|---|
| | May | June | July | August | September | Seasonal avg. |
| S-2 | 57 | 71 | 63 | 56 | 56 | 61 |
| Merion | 60 | 69 | 66 | 61 | 64 | 64 |
| Delta | 73 | 80 | 80 | 78 | 74 | 75 |
| Common | 74 | 87 | 73 | 66 | 65 | 73 |
| LSD 5% | 12 | 3 | 4 | 6 | 4 | ---------- |

(LSD is a common abreviation for "Least Significant Difference" which is the statistical measure used to compare two means.)

*Table 3.—Monthly Average Yield of Grass Clipping of S-2 and Other Bluegrasses from Equal Areas Mowed at a 2 Inch Height Weekly—1961*

| Variety | Dry clippings removed (gms.) | | | | |
|---|---|---|---|---|---|
| | June | July | September | October | Seasonal avg. |
| S-2 | 27.0 | 28.1 | 32.1 | 29.6 | 29.7 |
| Merion | 28.0 | 29.1 | 49.9 | 64.6 | 42.9 |
| Delta | 30.5 | 30.3 | 46.5 | 38.0 | 36.6 |
| Common | 33.2 | 33.6 | 22.2 | 39.3 | 44.8 |
| LSD 5% | ---------- | ---------- | ---------- | ---------- | 12.7 |

*Table 4.—Monthly Average Yield of Grass Clippings of S-2 and Other Bluegrasses From Equal Areas Mowed at a 1⅜ inch height weekly—1962*

| Variety | Dry clippings removed (gms.) | | | | | |
|---|---|---|---|---|---|---|
| | May | June | July | August | September | Seasonal avg. |
| S-2 | 46.6 | 34.4 | 29.5 | 23.1 | 18.3 | 30.4 |
| Merion | 65.9 | 36.1 | 34.8 | 33.2 | 22.2 | 38.5 |
| Delta | 65.6 | 41.6 | 30.7 | 30.9 | 20.8 | 37.9 |
| Common | 62.7 | 35.9 | 30.4 | 29.3 | 21.8 | 36.0 |
| LSD 10% | ---------- | ---------- | ---------- | ---------- | ---------- | 7.1 |

*Table 5.—Monthly Average Yield of Grass Clippings for S-2 Compared to Other Bluegrasses From Equal Areas Mowed at a 2 inch height Every 14 Days—1962*

| Variety and blend | Dry clippings removed (gms.) | | | | |
|---|---|---|---|---|---|
| | July | August | September | October | Seasonal avg. |
| S-2 | 18.2 | 12.8 | 11.4 | 10.6 | 13.2 |
| Merion | 18.5 | 12.2 | 15.8 | 20.6 | 15.9 |
| Newport | 22.7 | 14.0 | 16.0 | 14.6 | 16.8 |
| Park | 23.9 | 21.3 | 27.8 | 20.8 | 23.4 |
| Beaumont | 27.4 | 12.4 | 20.1 | 17.1 | 19.2 |
| LSD 5% | ---------- | ---------- | ---------- | ---------- | 8.3 |

*Table 6.—Relative Comparison of Leaf Spot Disease Levels for S-2 and Other Bluegrass Varieties*

| Variety | Leaf spot ranking [1] | |
|---|---|---|
| | Exp #1-1960-61 | Exp #2-1960-61-62 |
| S-2 | 9 | 9 |
| Merion | 9 | 8 |
| Delta | 7 | 7 |
| Common | 6 | 7 |
| LSD 5% | 1 | 1 |

[1] Ranking scale:
10 = no evidence of disease activity.
1 = disease activity very evident.

*Table 7.—Relative Comparison of Stem-Rust Disease Level for S-2 and Other Bluegrass Varieties in 1961*

| Variety | Rust disease ranking [1] | |
|---|---|---|
| | Exp #1 | Exp #2 |
| S-2 | 9 | 10 |
| Merion | 1 | 2 |
| Delta | 9 | 10 |
| Common | 9 | 10 |

[1] Ranking Scale:
10 = no evidence of disease activity.
1 = disease activity very evident.

*Table 8.—Relative Comparison of Dollarspot Disease Level for S-2 and Other Bluegrass Varieties in 1960 and 1961*

| Variety | Dollarspot ranking [1] |
|---|---|
| S-2 | 8 |
| Park | 5 |
| Campus | 8 |
| Delta | 8 |
| LSD 5% | NS |

[1] Ranking Scale:
10 = no evidence of disease activity.
1 = disease activity very evident.

*Table 9.—Turf Density Comparisons for S-2 and Other Bluegrasses—1961–62*

| Variety | Density ranking [1] | | | |
|---|---|---|---|---|
| | Spring | Summer | Fall | Seasonal avg. |
| S-2 | 8 | 8 | 10 | 9 |
| Merion | 8 | 8 | 9 | 8 |
| Delta | 8 | 9 | 8 | 8 |
| Common | 8 | 8 | 9 | 8 |
| LSD 5% | NS | NS | 1 | ---------- |

[1] Ranking Scale:
10 = highest density.
1 = lowest density.

*Table 10.—Density of S-2 and Other Bluegrass Varieties as Reflected in Plant Counts From Turf Plots Mowed at 1½ Inches—1961*

| Variety | Blade counts (avg. 1⅞" dia. sample) |
|---|---|
| S-2 | 37 |
| Merion | 28 |
| Delta | 24 |
| Common | 27 |
| LSD 5% | 3 |

*Table 11.—Turf Color Comparisons for S-2 and Other Bluegrass Varieties—1960-61*

| Variety | Color ranking [1] | | | |
|---|---|---|---|---|
| | Spring | Summer | Fall | Seasonal avg. |
| S-2 | 9 | 8 | 5 | 7 |
| Merion | 8 | 8 | 5 | 7 |
| Delta | 5 | 7 | 6 | 6 |
| Common | 5 | 6 | 7 | 6 |
| LSD 5% | 3 | 1 | NS | ---------- |

[1] Ranking Scale:
10=darkest green.
1=lightest green.

*Table 12.—Turf Color Comparisons for S-2 and Other Bluegrass Varieties—1961-62*

| Variety | Color ranking [1] | | | |
|---|---|---|---|---|
| | Spring | Summer | Fall | Seasonal avg. |
| S-2 | 10 | 7 | 8 | 8 |
| Merion | 9 | 7 | 6 | 8 |
| Delta | 7 | 5 | 6 | 6 |
| Common | 7 | 6 | 7 | 7 |
| LSD 5% | NS | NS | 1 | ---------- |

[1] Ranking Scale:
10=darkest green.
1=lightest green.

*Table 13.—Comparison of S-2 and Other Bluegrass Varieties Under Drought Conditions—1962*

| Variety | Level of wilting at mowing height [1] | | |
|---|---|---|---|
| | 1" | 2" | Avg. |
| S-2 | 3.0 | 3.0 | 3.0 |
| Merion | 2.9 | 3.0 | 2.95 |
| Delta | 1.8 | 2.0 | 1.90 |
| Common | 1.5 | 1.8 | 1.65 |
| LSD 5% | ---------- | ---------- | .90 |

[1] Ranking scale:
3 = no evidence of wilting.
1 = severe wilting.

*Table 14.—Number of Caryopses With Attached Lemma and Palea Per Pound for S-2 and Other Bluegrasses—1962*

| Variety | Number per pound [1] | Standard error |
|---|---|---|
| S-2 | 1,520,885 | 59,728 |
| Merion | 1,911,300 | 65,407 |
| Delta | 1,962,050 | 75,682 |
| Newport | 1,204,945 | 90,945 |
| Beaumont | 1,530,640 | 81,797 |
| Common | 1,573,325 | 83,836 |

[1] Number per pound-average based on 10-500 floret samples.

What is claimed and desired to be secured by Letters Patent is:

The variety of bluegrass plant, substantially as shown and described herein, characterized particularly by dark green color under average lawn conditions, early spring color and prolonged retention of color through summer and into fall, dense growth, less vertical growth, high resistance to common grass diseases, and ability to survive under drought conditions.

No references cited.